(12) United States Patent
Uhlemann

(10) Patent No.: US 9,297,906 B2
(45) Date of Patent: Mar. 29, 2016

(54) DOSIMETER, THERAPEUTIC APPARATUS, AND COMPUTER PROGRAM PRODUCT FOR MEASURING RADIATION DOSAGE TO A SUBJECT DURING MAGNETIC RESONANCE IMAGING

(75) Inventor: Falk Uhlemann, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 392 days.

(21) Appl. No.: 13/820,851

(22) PCT Filed: Sep. 7, 2011

(86) PCT No.: PCT/IB2011/053911
§ 371 (c)(1),
(2), (4) Date: Mar. 28, 2013

(87) PCT Pub. No.: WO2012/032477
PCT Pub. Date: Mar. 15, 2012

(65) Prior Publication Data
US 2013/0218001 A1  Aug. 22, 2013

(30) Foreign Application Priority Data
Sep. 9, 2010  (EP) .................................... 10175972

(51) Int. Cl.
*A61B 5/055* (2006.01)
*G01T 1/02* (2006.01)
*A61N 5/10* (2006.01)
*G01T 1/04* (2006.01)
*A61B 5/00* (2006.01)
*G01R 33/48* (2006.01)

(52) U.S. Cl.
CPC . *G01T 1/02* (2013.01); *A61B 5/055* (2013.01); *A61B 5/4836* (2013.01); *A61N 5/1049* (2013.01); *A61N 5/1067* (2013.01); *A61N 5/1071* (2013.01); *A61N 5/1077* (2013.01); *G01R 33/4808* (2013.01); *G01T 1/04* (2013.01); *A61N 2005/1055* (2013.01); *A61N 2005/1072* (2013.01)

(58) Field of Classification Search
CPC ................. A61B 5/055; A61B 5/4836; A61N 2005/1055; A61N 2005/1072; A61N 5/1049; A61N 5/1067; A61N 5/1071; A61N 5/1077; G01R 33/4808; G01T 1/02; G01T 1/04
See application file for complete search history.

(56) References Cited

U.S. PATENT DOCUMENTS

| 4,350,607 A | 9/1982 | Apfel |
| 5,633,584 A | 5/1997 | Maryanski et al. |

(Continued)

FOREIGN PATENT DOCUMENTS

| CN | 2369254 Y | 3/2000 |
| CN | 101015723 Y | 8/2007 |

(Continued)

OTHER PUBLICATIONS

Austerlitz, C., et al.; Quality assurance of HDR 192Ir sources using a Fricke dosimeter; 2007; Med. Phys.; 34(4) 1348-1353.

(Continued)

*Primary Examiner* — Ruth S Smith

(57) ABSTRACT

A dosimeter measures radiation dosage to a subject during a magnetic resonance imaging guided radiation therapy session. The dosimeter includes an outer surface configured to receive a surface of the subject, and discrete cells. Each of the discrete cells is filled with a magnetic resonance radiation dosimeter.

13 Claims, 5 Drawing Sheets

(56) References Cited

U.S. PATENT DOCUMENTS

| | | | |
|---|---|---|---|
| 6,662,036 B2 * | 12/2003 | Cosman | 600/411 |
| 7,399,977 B2 | 7/2008 | Rink et al. | |
| 7,491,942 B2 | 2/2009 | Black et al. | |
| 7,495,224 B2 | 2/2009 | Widener et al. | |
| 7,557,353 B2 | 7/2009 | Black et al. | |
| 7,574,251 B2 * | 8/2009 | Lu et al. | 600/427 |
| 2006/0002519 A1 | 1/2006 | Jenkins et al. | |
| 2008/0149835 A1 * | 6/2008 | Moritake et al. | 250/336.1 |
| 2010/0049030 A1 | 2/2010 | Saunders et al. | |

FOREIGN PATENT DOCUMENTS

| | | | |
|---|---|---|---|
| WO | 2004080522 A1 | 9/2004 | |
| WO | 2006130630 A2 | 12/2006 | |
| WO | 2008120117 A2 | 10/2008 | |
| WO | 2009063246 A2 | 5/2009 | |

OTHER PUBLICATIONS

Cavinato, C. C., et al.; Spectrophotometric response of the Fricke gel dosimeter developed at IPEN for clinical electron beams; 2010; Proc. of Third European IRPA Congress, Helsinki, Finland; pp. 1-7.

Galante, A. M. S., et al.; MRI study of radiation effect on Fricke gel solutions; 2008; Radiation Measurements; 43:550-553.

Tomatis, S., et al.; Gel-layer dosimetry for dose verification in intensity modulated radiation therapy; 2007; Nuclear Instruments and Methods in Physics Research Section A: Accelerators, Spectrometers, Detectors and Associated Equipment; 580:506-509.

* cited by examiner

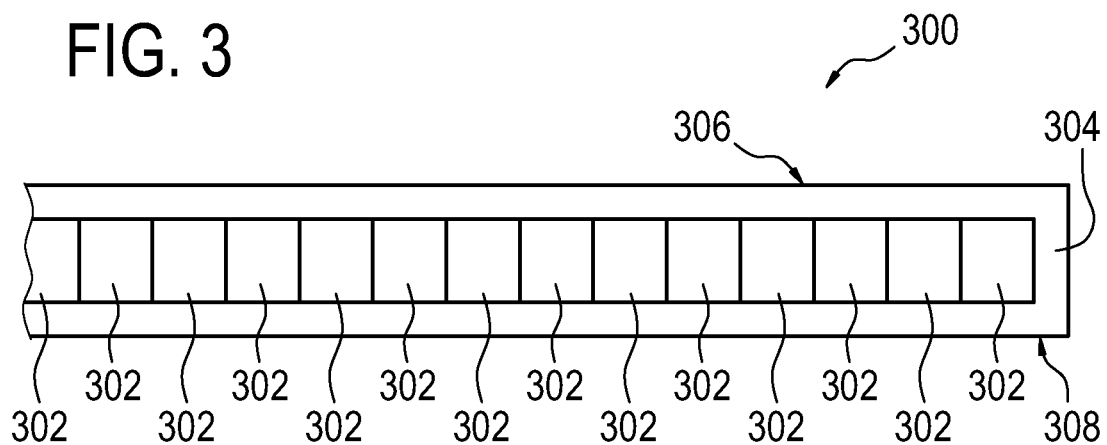
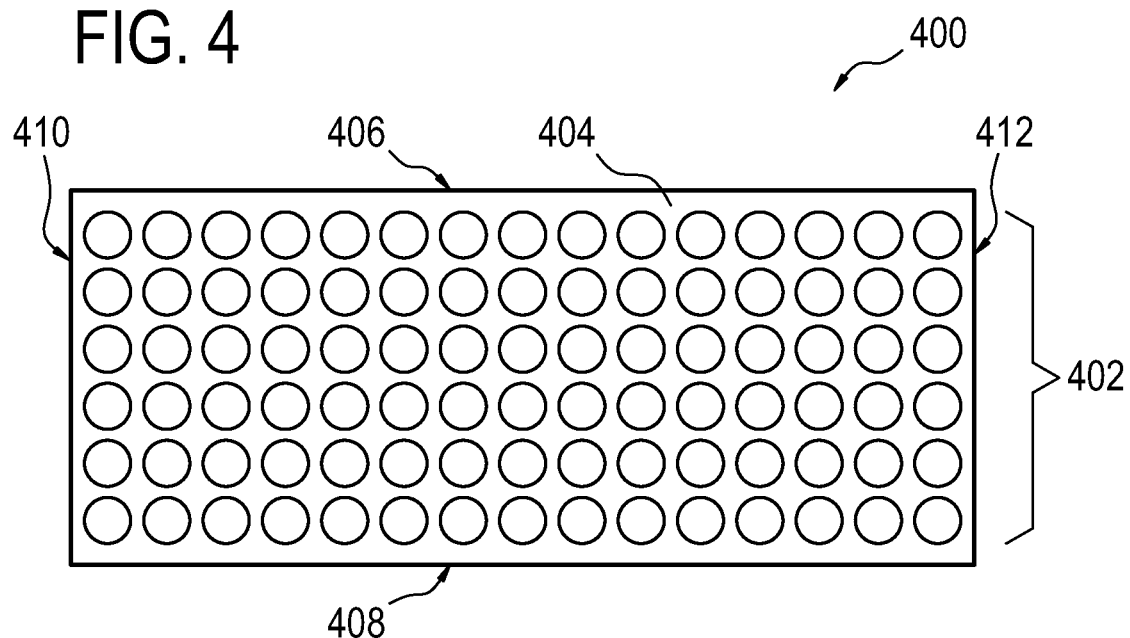

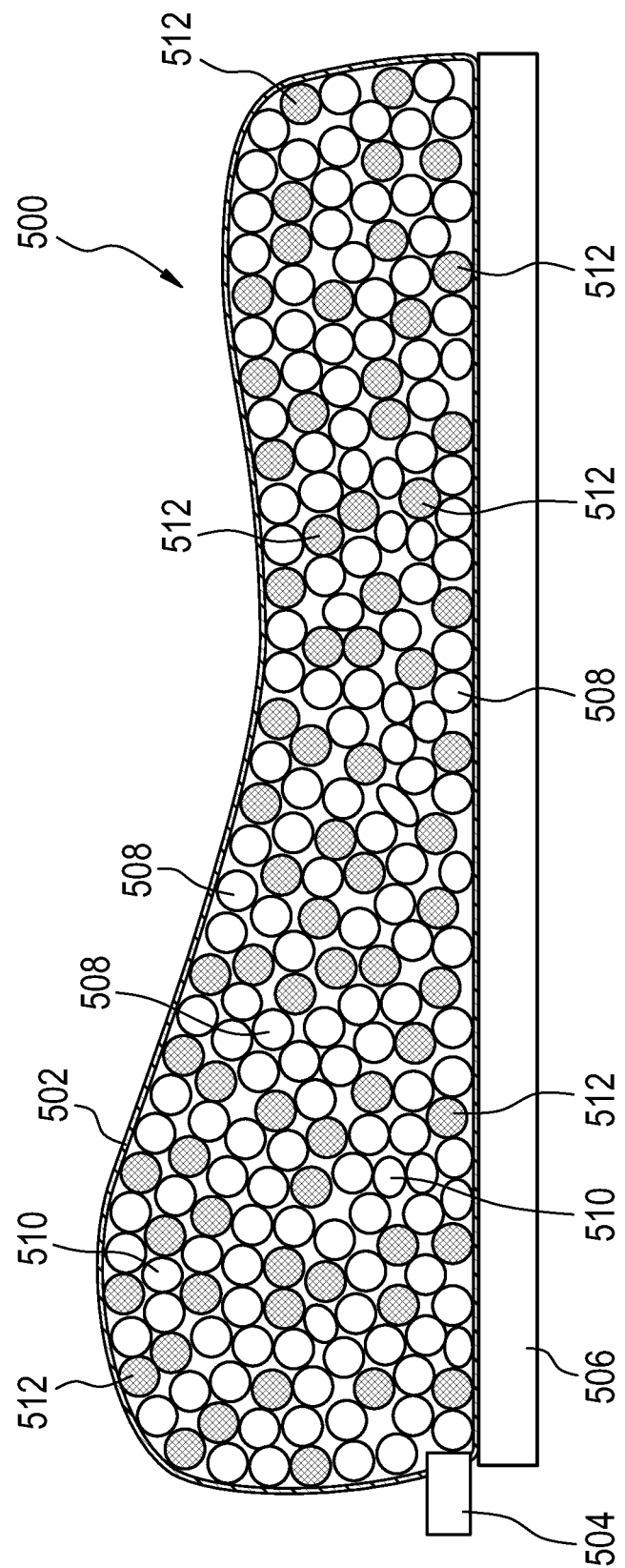

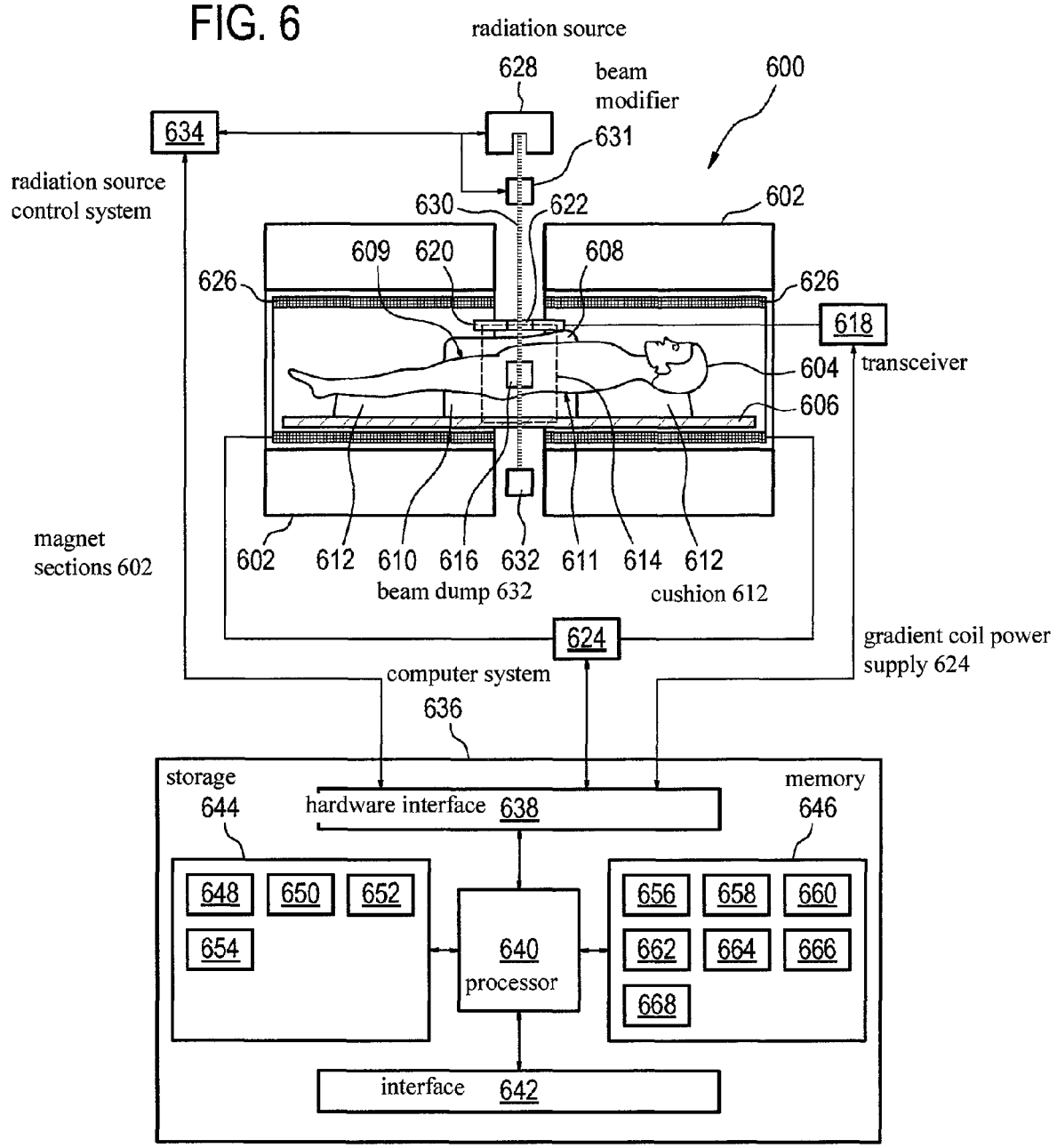

DOSIMETER, THERAPEUTIC APPARATUS, AND COMPUTER PROGRAM PRODUCT FOR MEASURING RADIATION DOSAGE TO A SUBJECT DURING MAGNETIC RESONANCE IMAGING

TECHNICAL FIELD

The invention relates to radiation dosimetry, in particular to radiation dosimetry during magnetic resonance imaging.

BACKGROUND OF THE INVENTION

During radiotherapy (RT) treatments the radiation beam has to be focused on a well-defined target region and its dose has to be precisely controlled. To verify the accuracy of the radiotherapy treatment field relative to the patient, radiosensitive film, video vision systems, ion chambers and electronic portal imaging devices (EPIDs) are currently used for two-dimensional (real-time) monitoring of the applied dose. Additionally time-consuming regular quality assurance of (three-dimensional) radiation dose distribution has to be performed with specific phantoms.

Some of the relevant characteristics of currently used radiation treatment field verification/dosimetry techniques are:

Ion chamber (low resolution, slow, non-integrating dose measurement),
Video chain (cumbersome, not geometrically accurate, bad efficiency),
Film (critical work-flow, lower sensitivity than EPID),
EPID (expensive, dead-pixels).

U.S. Pat. No. 5,633,584 describes gel in a container in which a MRI visualizable permanent image is formed in response to ionizing radiation. The image is representative of the dose distribution of the energy to which the gel is exposed. The image can be used for dosimetric purpose; to provide reference standards for quality control of magnetic resonance imaging techniques and equipment; and as a three- or two-dimensional array detector in industrial radiography.

SUMMARY OF THE INVENTION

The invention provides for a dosimeter, a therapeutic apparatus, and a computer program product in the independent claims. Embodiments are given in the dependent claims The accuracy and reproducibility of the setup in clinical routine are very important for correct patient position determination but this is difficult to accomplish with the first three techniques due to construction related insufficient mechanical reproducibility, inherent inaccuracies of spatial radiation localization via field-edge detection and unreliable/tedious registration of anatomical landmarks.

With EPIDs a dose and geometry verification is possible (non integrating dose measurement) but additional imaging radiation exposure ("monitor dose units") is necessary for full treatment field imaging which increases the risk of cancer induction and is unfeasible for e.g. prostate imaging due to significant internal movement. Also, extra imaging time is needed and the EPID devices are expensive.

Magnetic resonance (MR) imaging system may be integrated with an RT device (MR-RT) which allows real-time MR-monitoring of the patient during radiotherapy. The co-registration of the two devices' coordinate systems allows a precise localization of points in RT and MR space. But this integration of MR and RT devices results in spatial constraints (e.g. magnet surrounding patient in bore) which make the use of currently used radiation visualization devices (e.g. portal imaging with EPID, see above) difficult if not impossible.

There is therefore a need for a better method visualizing or measuring radiation dosage for combined MR and RT devices. Embodiments of the invention may allow the measurement of the three-dimensional distribution of the applied dose in real-time using the MR device. It does not require additional imaging time or dose as current radiotherapy systems do with e.g. portal imaging. The used radiosensitive substances or dosimeters, in some embodiments, may be fully MR compatible and may not be hazardous.

Embodiments of the invention may also not be invasive, which is a significant advantage over the alternative radiosensitive contrast agents. The proposed dosimeter can easily be applied to various existing devices (e.g. patient fixation, covers, blankets) which may allow for a small, flexible, light-weight, very cost efficient and patient specific design. This may increase patient safety, comfort and clinical work-flow.

Due to very strict quality assurance and radiation monitoring regulations concerning RT treatments, the proposed invention is a potential enabler—if not prerequisite—for the approval and clinical application of future MR-RT devices.

The proposed invention may allow real-time three-dimensional dosimetry of patients undergoing radiotherapy in an MR-RT system. The merger of radiosensitive substances with existing devices enables a smooth clinical work-flow. Easy to use light-weight construction and flexibility of the design allow comfortable patient specific application.

Possible realizations for the radiosensitive substance are commercially available (e.g. well known polymer or Fricke-gels). These have proven to be suitable for dosimetric purposes because they exhibit a linear dose response over a wide dynamic range. They are currently employed for research and quality assurance purposes via irradiating them with conventional RT devices and subsequently transporting to and imaging with MR devices.

Fricke-gel is especially simple to prepare and has good tissue mimicking properties. Its physical properties can be adjusted by adding various substances.

To overcome problems of oxygen diffusion (which increases relaxation rate) and diffusion (which blurs the measurement) effects the substance can be confined in (flexible) microcapsules.

To achieve absolute dosimetry in some embodiments, constant quality of the substance and operating temperature may be ensured and reference measurements have to be conducted. These can be easily performed for a sample of each batch of produced material using the MR-RT machine.

Employing suitable post-processing (simple filtering and differential operations) the integrating nature of the substances due to irreversible processes can be compensated to achieve real-time imaging of the dose distribution.

Various realizations of the proposed dosimeter device are imaginable (e.g. patient fixation, blankets, (removable) patient table covers, patient-surrounding cover). Below the orthogonal cross-sectional views of a patient fixation device incorporating the radiosensitive substance are shown.

This is a similar design to currently used patient fixating devices employing evacuated patient beds: so called vacuum mattresses, vacuum pillows, or bean bags. But in this representation the "bag" is filled with the radiosensitive microcapsules. After the patient is correctly positioned on the loose (not evacuated) "bean bag" it is evacuated thereby fixing the capsules and consequently the patient into stable position as required by radiotherapy.

During the therapy the radiation source rotates around the patient and applies the planned dose while penetrating the said substance. This induces irreversible chemical reactions which can be visualized employing known MR imaging sequences in parallel to the radiation.

Via filtering and temporal differential reconstruction the applied dose can be calculated in real-time.

To reduce temperature drift effects of the gel a thermally insulating layer can be placed between patient and radiosensitive substance.

To minimize disposable material the radiosensitive substance can be placed in a layer close to the patient. This layer could then be detached from the patient fixation bed and replaced by a new one.

This layered design could be employed to surround the patient in the irradiated region. Via comparing the measured dose entering the patient and leaving the patient the actual absorption could be reconstructed and be used as additional verification of the treatment plan.

In some embodiments a device and method to perform radiometric therapy control and integrated dosimetric quality assurance measurements for magnetic resonance (MR) guided radiotherapy (RT) procedures using a radiosensitive substance, a dosimeter, is realizable.

This substance is confined within a structure partially surrounding or being located in the close proximity to the patient in the form of e.g. a vacuum mattress or a blanket.

This approach requires no additional radiation dose for imaging purposes, allows three-dimensional dose imaging in real-time and is fully MR compatible. Its small and flexible design permits easy patient specific customization (e.g. integration into patient fixation devices).

The used radiosensitive substances can be easily and inexpensively produced.

Conventional RT treatment field verification techniques (e.g., portal imaging detectors) cannot be used in MR-RT systems.

Due to very strict quality assurance and radiation monitoring regulations concerning RT treatments, the proposed invention is a potential enabler for the approval and clinical application of future MR-RT devices.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance data. This visualization can be performed using a computer.

A computer-readable storage medium as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

The term 'computer memory' is an example of a computer-readable storage medium. Computer memory is any memory which is directly accessible to a processor. Examples of computer memory include, but are not limited to: RAM memory, registers, and register files.

The term 'computer storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

The term 'a processor' encompasses an electronic component which is able to execute a program or machine executable instruction. References to the computing device comprising "a processor" should be interpreted as possibly containing more than one processor. The term computing device should also be interpreted to possibly refer to a collection or network of computing devices each comprising a processor. Many programs have their instructions performed by multiple processors that may be within the same computing device or which may even distributed across multiple computing device.

In the one aspect the invention provides for a dosimeter for measuring radiation dosage to a subject during a magnetic resonance imaging guided radiation therapy session. The dosimeter comprises an outer surface adapted for receiving a surface of the subject. In other words the dosimeter is designed to contact the surface of the subject. The dosimeter further comprises discreet cells filled with a magnetic resonance radiation dosimeter. A magnetic resonance radiation dosimeter as used herein encompasses a dosimeter for which the dosage is measured using magnetic resonance imaging or nuclear magnetic resonance. Examples of magnetic resonance radiation dosimeters include but are not limited to a Fricke Dosimeter and a polymer dosimeter. This embodiment is advantageous because discreet cells are filled with the magnetic resonance radiation dosimeter. The cell size can be chosen such that diffusion of the dosimeter material is limited by the size of the discreet cells. The use of discreet cells also may provide a structural support to the dosimeter. For instance, if the dosimeter was fashioned in the form of a blanket use of discreet cells allows the formation of a flexible sheet of the discreet cells with the magnetic resonance radiation dosimeter.

In another embodiment the dosimeter further comprises a thermal insulation layer between the outer surface and the discreet cells. This embodiment is particularly advantageous because if the subject has a temperature which is not identical to that of the magnetic resonance radiation dosimeter then the subject may heat or cool the magnetic resonance radiation dosimeter. Magnetic resonance radiation dosimeters such as a Fricke Dosimeter may be temperature sensitive. For instance if the subject is a mammal then the subject may have a tendency to heat the magnetic resonance radiation dosimeter and this would affect the accuracy of the measurements.

In another embodiment the dosimeter is a vacuum pillow. The dosimeter further comprises polystyrene foam balls. The discreet cells each comprise shells filled with the magnetic resonance radiation dosimeter. Within the vacuum pillow the discreet cells and the polystyrene foam balls are mixed. A vacuum pillow as used herein encompasses a pillow filled with compressible balls such as polystyrene foam balls. As air is pumped out of the vacuum pillow the covering compresses the polystyrene foam balls and the mild compression causes them to hold their shape. Vacuum pillows are typically used for medical treatments where it is advantageous if the subject is kept in the same position or does not move. For instance a subject may lie on a vacuum pillow and then the vacuum may be used to keep the vacuum pillow from changing shape. Integrating the dosimeter into the vacuum pillow is advantageous because the vacuum pillow and serves a synergistic purpose: it immobilizes or holds the patient steady at the same time as providing the dosimetric function.

In another embodiment the dosimeter is adapted to be mounted to a patient support of a magnetic resonance imaging system. This embodiment is advantageous because the dosimeter may be integrated or mounted to the patient support.

In another embodiment the dosimeter is a pad. The discreet cells are dispersed uniformly within the thermal insulation layer. For instance the dosimeter may be a foam pillow or cushion and the discreet cells may be dispersed uniformly within the foam which forms the pillow and also the thermal insulation pair. In this embodiment it may be realized in several different ways. For instance the discreet cells could just be randomly mixed into a foam which then solidifies. In other embodiments the discreet cells may for instance by spheres which are packed uniformly and then coated with a foam layer. For instance the discreet cells may be in a hexagonal close pack structure.

In another embodiment the dosimeter is a blanket. The discreet cells are arranged in a continuous layer and the thermal insulation layer surrounds the continuous layer. This embodiment is particularly advantageous because during a procedure the dosimeter may simply be placed under or on a subject.

In another embodiment the dosimeter comprises two parts. Each of the two parts has an outer surface adapted for receiving two opposing surfaces of the subject. This embodiment may be realized in several different ways. For instance the two parts may have alignment pins or other structures which fit together or have an interlocking connection. In other embodiments the two parts may simply be a lower cushion and an upper blanket.

In another embodiment the magnetic resonance dosimeter is a Fricke Dosimeter. This embodiment is advantageous because Fricke Dosimeters are well known and their ability to function as a dosimeter for ionizing radiation or being measured by nuclear magnetic resonance or magnetic resonance imaging is well known.

In another embodiment the magnetic resonance radiation dosimeter is a polymer dosimeter.

In another aspect the invention provides for a therapeutic apparatus. The therapeutic apparatus comprises a magnetic resonance imaging system adapted for acquiring a set of magnetic resonance data in an imaging zone. The therapeutic apparatus further comprises an ionizing radiation source adapted for directing a beam of ionizing radiation towards a target zone within a subject. The ionizing radiation source may be one of many different types. For instance the ionizing radiation source may be, but is not limited to: a gamma radiation system, a charged particle accelerator, a carbon nuclei radiation source, a proton beam radiation source, and an X-ray radiation source. The combination of the magnetic resonance imaging system and the ionizing radiation source is beneficial because the magnetic resonance imaging system may be used for guiding the ionizing radiation source. For instance magnetic resonance imaging images may be constructed from the magnetic resonance data and used to construct images which show the internal anatomy of the subject.

The therapeutic apparatus further comprises a computer system with a processor. The computer system functions as a control system for the therapeutic apparatus. It is understood herein that references to a computer system may actually refer to multiple computers or computer systems. For instance a computer system may represent a network of computer systems. It is also understood herein that references to a processor also may refer to multiple processors. For instance a single computer may have a multi-core or multiple processors and also the processors may be distributed amongst a collection of computer systems.

The therapeutic apparatus further comprises computer-readable storage medium containing machine-executable instructions for execution by the processor. Execution of the instructions causes the processor to perform the step of determining a position of the target zone. The position of the target zone may be performed in several different ways. For instance magnetic resonance data may be acquired by the magnetic resonance imaging system and anatomical data segmented from the resulting images may be used to determine the position at the target zone.

In other embodiments physical positioning systems such as a vacuum pillow and/or restraints may be used to position the patient. For instance initial imaging may be performed using other systems such as a CT system.

In other embodiments markers may be placed on the surface of the subject and these may be used to determine the position of the target zone. Execution of the instructions further causes the processor to perform the step of directing the beam of ionizing radiation into the target zone using the position of the target zone. The Ionizing radiation is directed such that the ionizing radiation passes through the dosimeter. The ionizing radiation passes through the target zone and the dosimeter. In this respect the dosimeter may therefore be used to estimate the amount of ionizing radiation passing through the target zone.

Execution of the instructions further cause the processor to perform the step of acquiring a set of magnetic resonance data from a dosimeter according to any one of the preceding claims using the magnetic resonance imaging system. The dosimeter is within the imaging zone.

Execution of the instructions further cause the processor to perform the step of calculating a dosage of ionizing radiation to the subject in accordance with the set of magnetic resonance data. In this step the magnetic resonance data acquired from the dosimeter is used to infer the dosage of radiation received by the subject. The amount of ionizing radiation may be calculated for that received in the target zone and it also may be calculated for regions of the subject surrounding the target zone. For instance during a therapy where cancer cells are targeted it is beneficial to understand or have an accurate knowledge of the amount of radiation received by healthy tissue.

In another embodiment the set of magnetic resonance data is acquired and the dosage is calculated simultaneously to the step of directing the beam of ionizing radiation. Execution of the instructions further cause the processor to adjust either the positioning, shape and/or intensity of the radiation beam in accordance with the dosage. These alterations in the radiation beam may be achieved differently depending upon the type of radiation beam. For example for charged particles, magnetic fields, charged particle optics, collimators, and attenuators may be used to modify the radiation beam. Physically moving the radiation source may also have an effect on the radiation beam. This embodiment is particularly advantageous because the dosage of ionizing radiation is used to adjust or guide positioning and/or intensity of the radiation beam. For instance the position of the radiation beam may be adjusted to reduce damage to healthy tissue.

In another embodiment the dosage of ionizing radiation in the target zone is calculated in accordance with a set of magnetic resonance data.

In another embodiment the instructions further cause the processor to adjust either the positioning, shape and/or intensity of the radiation beam in accordance with the dosage of ionizing radiation in the target zone.

In another embodiment the step of determining the position of the target zone is accomplished by using a registered coordinate system determined preoperatively.

In another embodiment the step of determining the position of the target zone is accomplished by determining the position of the target zone in accordance with the magnetic resonance data.

In another embodiment the instructions further cause the processor to perform the step of calculating a dosage distribution map in the subject in accordance with the magnetic resonance data. As used herein a dosage distribution map encompasses a map which maps the dosage in different regions of the subject. The dosage distribution map may be calculated by using knowledge of the position of the ionizing radiation beam at a particular time as well as a knowledge of the dosage as measured by the dosimeter as a function of time also. In some embodiments attenuation or absorption of the radiation by the subject may be calculated in accordance with the magnetic resonance data. That is to say the magnetic resonance data may be used for reading out the dosage received by the dosimeter as well as estimating the type of tissue that the radiation beam is passing through. This knowledge of the anatomy of the subject may be used for helping to calculate the dosage distribution map.

In another embodiment the instructions further cause the processor to perform the step of directing the ionizing radiation through a second dosimeter according to an embodiment of the invention. The second dosimeter is within the imaging zone. The instructions further cause the processor to perform the step of calculating a dose absorption map in the subject in accordance with the magnetic resonance data. A dose absorption map is a map or image which shows which regions of the subject absorb a particular dosage of radiation. The dose absorption map may be calculated because the dosage received by one of the dosimeters may be subtracted from the second one. This gives a direct measurement of how much ionizing radiation is absorbed by the subject. The dose absorption map may also be used to calculate the dosage distribution map in the subject.

In another aspect the invention provides for a computer program product comprising machine-executable instructions for execution by a processor of a computer system for controlling a therapeutic apparatus according to an embodiment of the invention. The therapeutic apparatus comprises a magnetic resonance imaging system adapted for acquiring a set of magnetic resonance data in an imaging zone. The therapeutic apparatus further comprises an ionizing radiation source adapted for directing a beam of ionizing radiation towards a target zone within a subject. The imaging zone comprises the target zone. Execution of the instructions causes the processor to perform the step of determining a position of the target zone. Execution of the instructions further causes the processor to perform the step of directing the beam of ionizing radiation towards the target zone using the position of the target zone. Execution of the instructions further cause the processor to perform the step of acquiring a set of magnetic resonance data from a dosimeter according to any one of the preceding claims using the magnetic resonance imaging system. Execution of the instructions further cause the processor to perform the step of calculating the dosage of ionizing radiation to the subject in accordance with the set of magnetic resonance data.

BRIEF DESCRIPTION OF THE DRAWINGS

In the following preferred embodiments of the invention will be described, by way of example only, and with reference to the drawings in which:

FIG. 3 shows an embodiment of a dosimeter according to the invention;

FIG. 4 shows a further embodiment of a dosimeter according to the invention;

FIG. 5 shows a further embodiment of a dosimeter according to the invention;

FIG. 6 shows a diagram which illustrates a therapeutic apparatus according to the invention.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
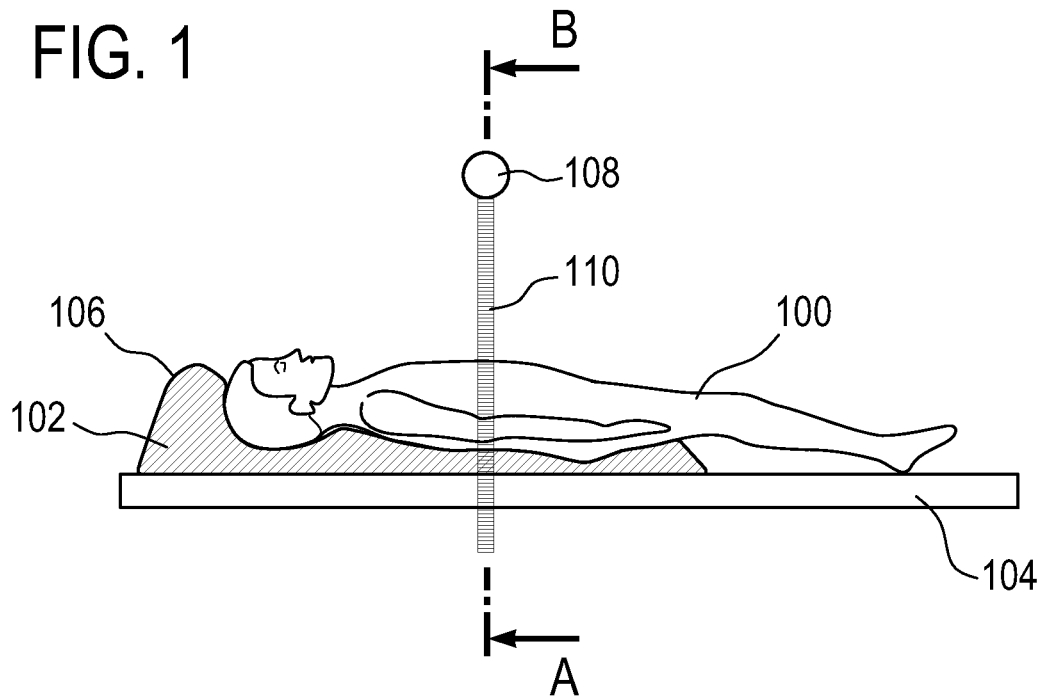
FIG. 1 illustrates the usage of a dosimeter according to an embodiment of the invention.
Figure 2:
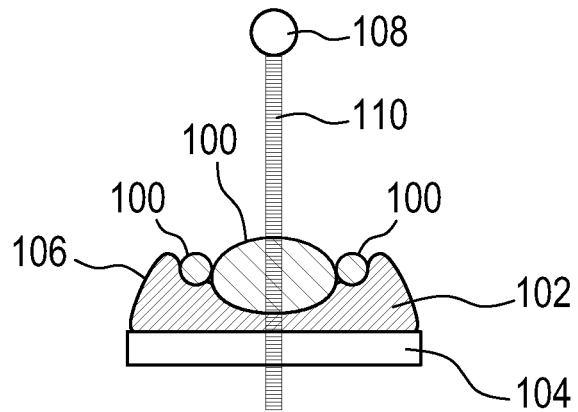
FIG. 2 shows a cross sectional view of the image shown in FIG. 1.

FIGS. 1 and 2 are used to illustrate the usage of a dosimeter according to an embodiment of the invention. FIG. 1 shows a side view of a subject reposing on a subject support 104. There is a dosimeter 102 between the subject and the subject support 104. The dosimeter 102 is in the form of a vacuum pillow or cushion for the subject 100 to repose upon. FIG. 2 is identical to that of FIG. 1 except in FIG. 2 a cross-section of the line marked AB in FIG. 1 is shown in FIG. 2. The dosimeter 102 is shown as having an outer thermal insulation layer 106 which thermally isolates the dosimeter 102 from the subject 100. Along the cross-section line AB there is a radiation source 108 which generates a beam of ionizing radiation 110. The ionizing radiation 110 is shown as passing through the subject 100, the dosimeter 102 and the subject support 104. In particular FIG. 2 illustrates that the radiation passing through the subject 100 also passes through the dosimeter 102. Since the radiation also passes through the dosimeter 102 the dosimeter 102 may be used to make an accurate determination of the ionizing radiation 110 that passes through the subject 100.

FIG. 3 shows an embodiment of a dosimeter 300 according to the invention. In this dosimeter 300 there is a collection of cells 302 which are arranged in a continuous layer. To form this continuous layer for example the discreet cells may be squares, hexagons or other shapes which are placed in a continuous layer. In some embodiments the discreet cells 302 are in full contact with each other. In other embodiments there is a spacing between the discreet cells 302. Surrounding the continuous layer of discreet cells 302 is a thermal insulation layer 304. The embodiment shown in FIG. 3 is essentially a pad or blanket. The use of the discreet cells 302 forming a continuous layer allows the dosimeter 300 to be flexible. The thermal insulation layer 304 may be used to thermally isolate the discreet cells 302 from a subject. The dosimeter 300 shown in FIG. 3 has two different outer surfaces, outer surface 306 and 308 which may be brought into contact with the surface of a subject.

FIG. 4 shows an alternative embodiment of a dosimeter 400 according to an embodiment of the invention. In the embodiment shown in FIG. 4 the dosimeter 400 is a pad or pillow. There are discreet cells 402 filled with a magnetic resonance radiation dosimeter. The discreet cells 402 are dispersed throughout the body of the dosimeter. The thermal insulation layer 404 also serves as the structure of the dosimeter 400. The discreet cells 402 are dispersed within the thermal insulation layer 404. For instance the thermal insulation layer 404 may be a foam. For instance to construct the dosimeter of FIG. 4 small spheres or shells filled with the magnetic resonance radiation dosimeter may be mixed into a foam and then the foam is set. The view shown in FIG. 4 is a cross-sectional cut through the dosimeter 400. The dosimeter shown in FIG. 4 has four outer surfaces, 406, 408, 410 and 412 which may come into contact and act as an outer surface adapted for receiving a surface of a subject.

FIG. 5 shows an example of a dosimeter 500 according to an embodiment of the invention. In this embodiment the dosimeter 500 is in the form of a vacuum pillow. The vacuum pillow has an outer shell 502 which also functions as a thermal insulation layer. Through a vacuum port 504 air or other gas may be pumped out of the vacuum pillow. When this happens the outer shell 502 compresses polystyrene foam 508 balls located within the vacuum pillow. The vacuum pillow 500 is shown as being mounted on an optional support 506. In this example the support 506 may be designed such that it interlocks with a patient support on a magnetic resonance imaging system. In the interior of the vacuum pillow there are the polystyrene foam balls 508 and shells 512 filled with magnetic resonance radiation dosimeter. The outer shell 502 compresses the polystyrene foam balls. Also shown are several polystyrene foam balls 510 which are under compression. In this embodiment it can be seen that by mixing small shells or balls filled with magnetic resonance radiation dosimeter into the vacuum pillow a combined vacuum pillow and dosimeter may be constructed. In this Fig. the polystyrene foam balls 508, 510 are shown as being unfilled circles. The shaded circles 512 represent the shells filled with magnetic resonance radiation dosimeter. Due to the large number of polystyrene balls 508, 510 and a large number of shells 512 not all are labeled. The view shown in FIG. 5 is a cross-sectional view cut through the vacuum pillow.

FIG. 6 shows an example of a therapeutic apparatus 600 according to an embodiment of the invention. The therapeutic apparatus comprises a magnetic resonance imaging system and a radiation source 628. In the embodiment shown in FIG. 6 the magnetic resonance imaging system comprises a split magnet 602 magnet. In other embodiments the magnet may be a so called open or toroidal magnet or may be a normal cylindrical magnet. The magnet sections 602 are cryogenically cooled superconducting magnets. Within the bore of the magnet 602 a subject 604 is reposing on a subject support 606. There is a first dosimeter 608 in contact with a first surface 609 of the subject 604.

Between the subject 604 and the subject support 606 there is a second dosimeter 610. The second dosimeter 610 is in contact with a second surface 611 of the subject 604. Adjacent to the second dosimeter 610 are two cushions 612 which are also used to support the subject 604. The magnets 602 have an imaging zone 614 which images a portion of the subject 604 and a portion of the first dosimeter 608 and the second dosimeter 610. Also within the subject 604 there is a target zone 616.

The magnetic resonance imaging system also comprises a radio frequency transceiver 618. The radio frequency transceiver may be in some embodiments replaced by a separate transmitter and receiver. The radio frequency transceiver is connected to a radio frequency coil 620. The radio frequency coil is for acquiring magnetic resonance data. The radio frequency coil 620 is shown as having a passage 622 for ionizing radiation 630 to pass through. The magnetic resonance imaging system also comprises a gradient coil power supply 624. Each of the magnet sections 602 has a section of a split gradient coil 626. The gradient coil power supply 624 supplies current to each section of the split gradient coil 626.

The therapeutic apparatus 600 also comprises a radiation source 628. The radiation source 628 is representative of many different types of radiation sources. For instance the radiation source 628 could generate gamma radiation, X-ray radiation, charged particles, carbon nuclei, protons and X-rays. The ionizing radiation 630 is shown as originating in the radiation source 628, passing through an optional beam modifier 631, passing through the first dosimeter 608, passing through the subject 604, passing through the target zone 616, passing through the second dosimeter 610 and then finally entering into a beam dump 632. The radiation source 628 and the beam modifier are shown as being controlled by a radiation source control system 634. The radiation source control system 634 may generate control commands for the beam modifier 631 and the radiation source 628. The beam modifier 631 comprises components for beam shaping, attenuation, and/or path correction. The beam modifier may also contain means for physically moving or adjusting the ionizing radiation beam 630. For instance, the beam modifier 631 may also include beam objects and collimators for the radiation source. The beam modifier 631 may include a multi leaf collimator to provide conformal shaping of the ionizing radiation 630. The radiation source control system 634, the radio frequency transceiver 618 and the gradient coil power supply 624 are all shown as being connected to a hardware interface 638 of a computer system 636.

The computer system 636 functions as the control system for the therapeutic apparatus 600. The computer system 636 further comprises a processor which is connected to the hardware interface 638 and a user interface 642. The user interface 642 comprises components and interfaces adapted for allowing an operator to interact with the computer system 636. For instance the user interface 642 may comprise a keyboard and mouse. The user interface 642 may also comprise a display for displaying images and control messages for the therapeutic apparatus 600. The processor 640 is also shown as being connected to computer storage 644 and computer memory 646.

The computer storage 644 is shown as containing magnetic resonance data 648. The magnetic resonance data 648 has been acquired by the magnetic resonance imaging system. The computer storage 644 is shown as further containing a magnetic resonance image 650. The magnetic resonance image 650 is reconstructed from the magnetic resonance data 648. The computer memory 644 is shown as further containing a dosage distribution map. The dose distribution map 652 has been calculated using the magnetic resonance data 648. The computer storage 644 is shown as further containing a dose absorption map 654 which has also been calculated from the magnetic resonance data 648.

The computer memory 646 is shown as containing a magnetic resonance imaging system control module 656. The magnetic resonance imaging system control module 656 controls the operation and function of the magnetic resonance imaging system. The computer memory 646 is shown as further containing a radiation source control module 658. The radiation source control module 658 contains software which generates control codes which are sent via the hardware interface 638 to the radiation source control system 634. The computer memory 646 is shown as further containing a target zone location module 660. The target zone location module 660 in some embodiments is able to use the magnetic resonance image 650 for determining the location of the target zone 616. In other embodiments the target zone location module 660 takes external data or reference points and uses this to locate the target zone 616.

The computer memory 646 is shown as further containing a magnetic resonance imaging reconstruction module 662. The magnetic resonance imaging reconstruction module 662 takes the magnetic resonance data 648 and reconstructs the magnetic resonance image 650. The computer memory 646 is shown as further containing a dosage calculation module 664. The dosage calculation module is able to calculate a dosage in the target zone 616 and/or in surrounding regions of the subject 604 using the magnetic resonance data 648. The computer memory 646 is shown as further containing a dose distribution map calculation module 666. The dose distribution map calculation module 666 uses the magnetic resonance data 648 to calculate the dose distribution map 652. The dose distribution map calculation module 666 uses magnetic resonance data acquired from the first 608 and/or second 610 dosimeter. The computer memory 646 is shown as further containing a dose absorption map calculation module 668. The dose absorption map calculation module 668 uses the magnetic resonance data 648 to calculate the dose absorption map 654. It should be noted that other embodiments are possible. For instance, the control of the radio therapy and the magnetic resonance imaging systems may be separate. As was noted earlier a single computer system and/or processor may represent multiple computer systems and/or processors. Additionally, the dose calculation and modification of the radiation therapy plan or treatment plan may be performed by separate computer systems.

To image the gels, gels can be scanned using an 8-echo multiple-spin-echo sequence with echo spacing echo time TE=35 ms, repetition time TR=345 ms and four repetitions (slice thickness: 6 mm, field of view FOV=192×192 mm$^2$, pixel size: 1.5×1.5 mm$^2$) resulting in a total acquisition time of 2 min 57 s per slice.

To obtain images the gels can also be scanned using a multiple spin-echo sequence with phase alternating-phaseshift (PHAPS) and 32 equidistant echo times (1.5 Tesla whole body scanner, TE=20-640 msec.; TR=11 sec; FOV=120×120 mm$^2$; matrix size [MS]=256) Gradient trains allow to bring the eddy currents into a steady-state regime. The gradient scheme was set up to refocus the slice select gradient before the first 180° refocusing pulse thereby avoiding a sinusoidal modulation of values measured in the z-direction.

General requirements for an MR system capable of using a Fricke dosimeter may be:
- MR imaging and quality control procedures for imaging should be available
- high-resolution dose maps with a sufficient SNR result in high demands on MR scanning of the gel (e.g. optimized sequence parameters, homogeneity of the RF)
- Compensation of eddy current effects by applying a gradient train in order to bring the eddy currents in a steady-state regime
- Compensation of temperature drifts via a centric gradient table reordering scheme (important data that determine the overall intensity in the base images was sampled in the beginning of the scanning cycle, final maps correspond to the initial temperature of the gel: therefore dose maps can be obtained from the final maps by using a calibration curve that is obtained at the same ambient temperature)
- Resolution: not too low to achieve reasonable SNR for dose measurement: typical pixel size 1.0-1.5 mm, slice thickness 3-5 mm (down to 1×0.5×0.5 mm$^3$ possible, at cost of SNR)

The Fricke gel or dosimeter can be used to detect ionizing radiation because radiation causes oxidation of ferrous ions into paramagnetic ferric ions. This changes the spinspin-relaxation rate and the spinlattice-relaxation rate. The amount of ferric ions produced depends on the energy being absorbed. In Fricke gels diffusion is negligible for t<3 h after radiation. In addition Fricke gels are a water equivalent over a broad dose range (good for tissue equivalent dose estimation). In Fricke gels oxidation processes stabilize after irradiation (up to 50 minutes) but this effect can be compensated by temporal calibration curves. The linear dose dependency of Fricke gel exists up to about 50-75 Gy. This is sufficient for clinical applications. New recipes have an inferior dose limit of about 0.006 Gy (aqueous Fricke solution less sensitive at low doses, saturates at about 500 Gy). Fricke gels are very simple to produce. In aqueous Fricke solutions the relaxivities and chemical yields of ferric ion are well enough established that NMR or MRI Fricke dosimetry can be used as an absolute dosimeter without the requirement for calibration. When incorporated into a gel matrix the details of the relaxation model become somewhat more complex. New recipes for Fricke gels allow long storage (PVAFX gels can be used even after 6 months (when kept cool) though it is not recommended).

Polymer dosimeters may consist of a gelatin hydrogel in which the comonomers acrylamide and N,N8-methylenebisacryHamide are dissolved. When the gel is irradiated, water molecules dissociate into free HO and H radicals that attack the double bonds of the comonomers. This initiation reaction is followed by a propagation reaction in which the comonomer radicals attack other comonomers, which then form a polymer chain. Because of the high fraction of the cross-linking agent, N,N8-methylenebisacrylamide relative to the fraction of acrylamide, the polymer structure is not linear, but forms small 3D polymer aggregates. The resulting reaction is dose dependent. As these polymer aggregates influence the mobility of the surrounding water molecules, the spatial dose distribution results in a spatial T2 distribution according to the theory of Bloembergen-Pound-Purcell.

Figure 7:
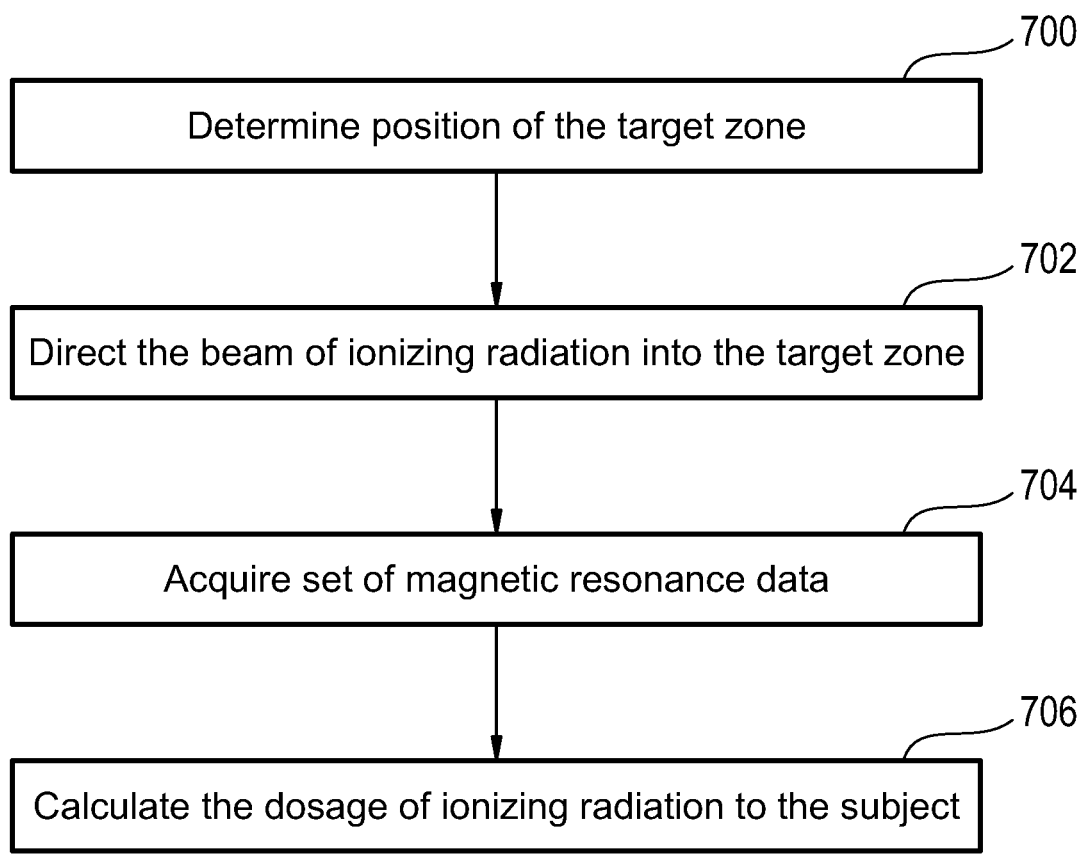
FIG. 7 shows a flow diagram which illustrates a method according to an embodiment of the invention.

Polymer dosimeters can be, depending on the composition, be as well water equivalent. Polymer dosimeters may have a higher dose sensitivity than Fricke gel, but can also be more difficult to produce than a Fricke gel. Many different recipes/material compositions exist for polymer gels, for instance:
- xylenol orange complexed with the ferrous ion (FBX)
- BANG (bis-acrylamide acrylamide nitrogen gelatin)-type gel is a gelatin hydrogel in which the comonomers acrylamide and N,N0-methylene-bisacrylamide are dissolved
- polyacrylamide and gelatine (PAG) gels
- MAGIC (methacrylic (MAA)
- ascorbic acid (AscA) in gelatine initiated by copper
- MAGAS (MAA, gelatine with AscA)
- MAGAT (MAA, gelatine and THPC) polymer gel dosimeters PAGAT is a normoxic PAG-type gel that uses tetrakis [hydroxymethyl] phosphonium chloride (THPC) to scavenge contaminating oxygen-free radicals PRESAGE is a radiochromic polymer dosimeter that consists of a clear polyurethane matrix containing a leuco-dye (leucomalachite green) that undergoes a color change when exposed to ionizing radiation FIG. 7 shows a flow diagram which illustrates an embodiment of a method according to the invention. In step 700 the position of the target zone is determined. The position of the target zone is determined through prior knowledge or is obtained using the magnetic resonance data. In step 702 the beam of ionizing radiation is directed into the target zone. In step 704 magnetic resonance data is acquired. In step 706 the dosage of ionizing radiation to the subject is calculated. The dosage of ionizing radiation to the subject is calculated by acquiring magnetic resonance data from a dosimeter according to an embodiment of the invention.

An example of a workflow for a computed magnet resonance and radio therapy device which uses radiometric patient fixation and the method illustrated in FIG. 7 is described below. Only work steps related to the use of the proposed device are shown. If necessary, the workflow can be interrupted at any stage and concluded at step 14.

1. Production of radiosensitive material (e.g. Fricke or polymer gel) under precisely controlled conditions including quality control and documentation of characteristics (e.g. production date, composition, batch number, sensitivity characteristics)
2. Transport and storage under controlled conditions (e.g. temperature, light, duration)
3. Verification and/or calibration of gel characteristics in test region (not within patient FOV) immediately before application employing (integrated) dosimeters (e.g. ionization chamber) depending on process reliability with regards to material production and storage
4. Application of radiometric material in proximity of patient
5. Set imaging parameters (i.e. MR sequence, geometry)
6. Prescan using MR to verify correct localization of patient, target region and radiometric material as well as suitable imaging settings (e.g. size of FOV)
7. Set and verify treatment parameters (e.g. patient, dose, timing, target zone)
8. Irradiate with simultaneous MR imaging of target and radiometric material (real time imaging). Depending on target localization FOV can be set and switched between target and radiometric material regions (e.g. interleaved imaging of target and regions in front of/behind target with respect to incident angle of radiotherapy beam
9. Use sensitivity characteristics, calibration results, treatment and imaging conditions (e.g. timing of irradiation, total duration, temperature, MR sequence settings) for conversion of image contrast (measured relaxation times) to dose information.
10. Calculate/reconstruct and display accumulated/integrated dose (post-processing, filtering (e.g. median), possibly taking organ motion into account)
11. Calculate/reconstruct and display incremental dose (e.g. per time interval, per irradiation angle) (possibly taking organ motion into account)
12. Verify treatment parameters and process (e.g. dose, patient/target position)
13. Repeat from step 8 until treatment is finished
14. Store treatment information (e.g. measured dose, radiometric material information, general clinical documentation) for quality assurance and possibly treatment plan adaptation purposes If necessary the above workflow can be interrupted at any stage and concluded at step 14.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A dosimeter for measuring radiation dosage to a subject during a magnetic resonance imaging guided radiation therapy session, the dosimeter comprising:
    a housing having a housing surface adapted for receiving a surface of the subject;
    discrete cells each filled with a magnetic resonance radiation dosimeter material; and
    foam balls, wherein the discrete cells and the foam balls are mixed in the housing.

2. The dosimeter of claim 1, wherein the dosimeter further comprises a thermal insulation layer between the housing surface and the discrete cells.

3. The dosimeter of claim 1, wherein the dosimeter is a pillow.

4. The dosimeter of claim 1, wherein the dosimeter comprises at least two cushions configured for mounting to a patient support of a magnetic resonance imaging system, and wherein the at least two cushions are configured to support the subject.

5. The dosimeter of claim 1, wherein the dosimeter comprises two parts, wherein each of the two parts has a respective surface adapted for receiving two opposing surfaces of the subject.

6. The dosimeter of claim 1, wherein the magnetic resonance radiation dosimeter material is one of a Fricke gel and a polymer gel.

7. A therapeutic apparatus comprising:
    a magnetic resonance imaging system adapted for acquiring a set of magnetic resonance data from an imaging zone;
    an ionizing radiation source adapted for directing a beam of ionizing radiation towards a target zone within a subject; a computer system with a processor;
    a non-volatile computer-readable storage medium containing machine-executable instructions for execution by the processor; and
    a dosimeter having a housing, the housing having a housing surface adapted for receiving a surface of the subject, discrete cells each filled with a magnetic resonance radiation dosimeter material, and foam balls, wherein the discrete cells and the foam balls are mixed in the housing, wherein execution of the instructions causes the processor to perform acts of:

determining a position of the target zone, directing the beam of ionizing radiation into the target zone using the position of the target zone, wherein the ionizing radiation is directed such that the ionizing radiation passes through the dosimeter, acquiring a set of magnetic resonance data from the dosimeter using the magnetic resonance imaging system, wherein the dosimeter is at least partially within the imaging zone, calculating a dosage of ionizing radiation to the subject in accordance with the set of magnetic resonance data acquired from the dosimeter.

8. The therapeutic apparatus of claim 7, wherein the acts of acquiring and calculating are performed simultaneously with the directing, wherein execution of the instructions further cause the processor to adjust at least one of a shape of the target zone, the position of the target zone and intensity of the radiation beam in accordance with the dosage.

9. The therapeutic apparatus of claim 8, wherein a dosage of ionizing radiation in the target zone is calculated in accordance with the set of magnetic resonance data from the dosimeter.

10. The therapeutic apparatus of claim 7, wherein the determining act is accomplished by any one of the following acts: using a registered coordinate system determined preoperatively, and determining the position of the target zone in accordance with the magnetic resonance data.

11. The therapeutic apparatus of claim 7, wherein the instructions further cause the processor to perform an act of calculating a dosage distribution map in the subject in accordance with the magnetic resonance data.

12. The therapeutic apparatus of claim 7, wherein the instructions further cause the processor to perform an act of directing the ionizing radiation through a second dosimeter, wherein the second dosimeter is at least partially within the imaging zone, wherein the instructions further cause the processor to perform an act of calculating a dose absorption map in the subject in accordance with the magnetic resonance data.

13. A non-transitory computer readable medium comprising machine executable instructions for execution by a processor of a computer system for controlling a therapeutic apparatus; wherein the therapeutic apparatus comprises a magnetic resonance imaging system adapted for acquiring a set of magnetic resonance data in an imaging zone; wherein the therapeutic apparatus further comprises an ionizing radiation source adapted for directing a beam of ionizing radiation towards a target zone within a subject; wherein the imaging zone comprises the target zone; and wherein execution of the instructions causes the processor to perform the acts of:

determining a position of the target zone;

directing the beam of ionizing radiation towards the target zone using the position of the target zone;

acquiring a set of magnetic resonance data from a dosimeter using the magnetic resonance imaging system, wherein the dosimeter comprises a housing having a housing surface adapted for receiving a surface of the subject, discrete cells each filled with a magnetic resonance radiation dosimeter material and foam balls, wherein the discrete cells and the foam balls are mixed in the housing;

calculating a dosage of ionizing radiation to the subject in accordance with the set of magnetic resonance data; and adjusting at least one of a shape of the target zone, the position of the target zone and intensity of the radiation beam in accordance with the dosage.

\* \* \* \* \*